(12) United States Patent
Sherman

(10) Patent No.: US 8,940,790 B2
(45) Date of Patent: Jan. 27, 2015

(54) STABLE PHARMACEUTICAL FORMULATIONS COMPRISING LUBIPROSTONE

(76) Inventor: Bernard Charles Sherman, Toronto (CA)

( * ) Notice: Subject to any disclaimer, the term of this patent is extended or adjusted under 35 U.S.C. 154(b) by 0 days.

(21) Appl. No.: 13/505,877

(22) PCT Filed: Nov. 3, 2010

(86) PCT No.: PCT/CA2010/001735
§ 371 (c)(1),
(2), (4) Date: Jul. 16, 2012

(87) PCT Pub. No.: WO2011/054087
PCT Pub. Date: May 12, 2011

(65) Prior Publication Data
US 2012/0270931 A1    Oct. 25, 2012

Related U.S. Application Data

(60) Provisional application No. 61/257,500, filed on Nov. 3, 2009.

(51) Int. Cl.
*A61K 31/352* (2006.01)
*A61K 31/558* (2006.01)
*A61K 47/34* (2006.01)

(52) U.S. Cl.
CPC .............. *A61K 31/558* (2013.01); *A61K 47/34* (2013.01)
USPC ........................................... 514/456

(58) Field of Classification Search
CPC ...... A61K 47/34; A61K 47/14; A61K 31/588
See application file for complete search history.

(56) References Cited

U.S. PATENT DOCUMENTS 4,409,239 A * 10/1983 Yu .................................. 514/530
6,414,016 B1 * 7/2002 Ueno ............................ 514/456
2007/0172522 A1 * 7/2007 Hirata et al. .................. 424/451
2007/0172523 A1   7/2007 Hashitera et al.

FOREIGN PATENT DOCUMENTS

WO         01/27099 A2    4/2012

OTHER PUBLICATIONS

Li et al. in Journal of Pharmaceutical Sciences 98(5), 1750-1764 (2008).*
Amitiza in www.rxlist.com/amitiza-drug.htm (retrieved from the internet Apr. 23, 2014).*
Lacy et al. in Clinical Interventions in Aging 2008:3(2) 357-364.*

* cited by examiner

*Primary Examiner* — Dennis Heyer
(74) *Attorney, Agent, or Firm* — The Webb Law Firm

(57) ABSTRACT

Provided is a pharmaceutical formulation comprising lubiprostone and at least one propylene glycol ester. The propylene glycol ester is typically selected from the group consisting of: propylene glycol mono-ester of lauric acid, propylene glycol mono-ester of caprylic acid, propylene glycol mono-ester of capric acid, propylene glycol di-ester of lauric acid, propylene glycol di-ester of caprylic acid and propylene glycol di-ester of capric acid.

7 Claims, No Drawings

STABLE PHARMACEUTICAL FORMULATIONS COMPRISING LUBIPROSTONE

TECHNICAL FIELD

This invention relates to the field of pharmaceutical formulations comprising Lubiprostone and more particularly to pharmaceutical formulations for oral administration comprising lubiprostone and a propylene glycol ester carrier.

BACKGROUND

Lubiprostone is a pharmaceutical that is sold under the trademark Amitiza™. Methods for stabilizing a lubiprostone by dissolving lubiprostone in a glyceride are known in the art. Also known are a method of stabilizing lubiprostone by admixing lubiprostone with a polyol and/or fatty acid ester other than glyceride and a composition obtained by the method. In addition a soft gelatin capsule formulation of lubiprostone obtained by incorporating lubiprostone in a soft gelatin capsule shell comprising gelatin and a polyol plasticizer is also known.

Also known in the art is a soft gelatin capsule formulation of lubiprostone, which comprises: a soft gelatin capsule shell comprising gelatin and sugar alcohol as a plasticizer, and a mixture comprising a 15-keto-prostaglandin compound and a pharmaceutically acceptable vehicle which is filled in the shell. By encapsulating the lubiprostone in the specified soft gelatin capsule shell, stability of the compound is significantly improved.

SUMMARY

This invention is based, at least in part, on the elucidation that pharmaceutical formulations comprising lubiprostone may be advantageously prepared using a carrier comprising at least one of: propylene glycol mono-esters of lauric acid, propylene glycol mono-esters of caprylic acid and propylene glycol mono-esters of capric acid as well as propylene glycol di-esters of lauric acid, caprylic acid and capric acid. Such carriers provide stability that is advantageous when compared to known suitable carriers used in pharmaceutical formulations for lubiprostone. Furthermore, such carriers provide suitable solubility for lubiprostone thereby providing further suitability for use in such pharmaceutical formulations.

Illustrative embodiments of the present invention provide a pharmaceutical formulation comprising lubiprostone and at least one propylene glycol ester selected from the group consisting of: propylene glycol mono-ester of lauric acid, propylene glycol mono-ester of caprylic acid, propylene glycol mono-ester of capric acid, propylene glycol di-ester of lauric acid, propylene glycol di-ester of caprylic acid and propylene glycol di-ester of capric acid.

Illustrative embodiments of the present invention provide a pharmaceutical formulation described herein wherein the at least one propylene glycol ester has a mono-ester content of 80% or less and a di-ester content of at least 20%.

Illustrative embodiments of the present invention provide a pharmaceutical formulation described herein wherein the at least one propylene glycol ester comprises Propylene Glycol Monocaprylate NF27 having a mono-ester content of between 55% to 80% and a di-ester content of between 20% to 45%.

Illustrative embodiments of the present invention provide a pharmaceutical formulation described herein wherein the at least one propylene glycol ester comprises Propylene Glycol Monocaprylate NF27 having a minimum mono-ester content of 90% and a maximum di-ester content of 10%.

Illustrative embodiments of the present invention provide a pharmaceutical formulation described herein wherein the at least one propylene glycol ester comprises Propylene Glycol Dicaprylate/Dicaprate NF27 having a di-ester content greater than a mono-ester content.

Illustrative embodiments of the present invention provide a pharmaceutical formulation described herein wherein the at least one propylene glycol ester comprises Propylene Glycol Monolaurate NF27 having a mono-ester content of between 45% to 70% and a di-ester content of between 30% to 55%.

Illustrative embodiments of the present invention provide a pharmaceutical formulation described herein wherein the at least one propylene glycol ester comprises Propylene Glycol Monolaurate NF27 having a minimum mono-ester content of 90% and a maximum di-ester content of 10%.

Illustrative embodiments of the present invention provide a pharmaceutical formulation described herein wherein the at least one propylene glycol ester comprises Propylene Glycol Dilaurate NF27 having a mono-ester content of 30% or less and a di-ester content of 70% or more.

Illustrative embodiments of the present invention provide a pharmaceutical formulation described herein wherein a by weight ratio of lubiprostone to propylene glycol ester is between from about 1:250000 to about 1:1000.

Illustrative embodiments of the present invention provide a pharmaceutical formulation described herein wherein a by weight ratio of lubiprostone to propylene glycol ester is about 3:12500.

Illustrative embodiments of the present invention provide a pharmaceutical formulation described herein wherein lubiprostone is dissolved in the at least one propylene glycol ester at a concentration of about 25 µg to about 1000 µg per gram.

Illustrative embodiments of the present invention provide a pharmaceutical formulation described herein wherein the at least one propylene glycol ester comprises Lauroglycol™ FCC.

Illustrative embodiments of the present invention provide a pharmaceutical formulation described herein wherein a by weight ratio of lubiprostone to Lauroglycol™ FCC is between from about 1:250000 to about 1:1000.

Illustrative embodiments of the present invention provide a pharmaceutical formulation described herein wherein a by weight ratio of lubiprostone to Lauroglycol™ FCC is about 3:12500.

Illustrative embodiments of the present invention provide a pharmaceutical formulation described herein wherein lubiprostone is dissolved in the Lauroglycol™ FCC at a concentration of about 25 µg to about 1000 µg per gram.

Illustrative embodiments of the present invention provide a pharmaceutical formulation described herein wherein the at least one propylene glycol ester comprises Capryol™ PGMC.

Illustrative embodiments of the present invention provide a pharmaceutical formulation described herein wherein a by weight ratio of lubiprostone to Capryol™ PGMC is between from about 1:250000 to about 1:1000.

Illustrative embodiments of the present invention provide a pharmaceutical formulation described herein wherein a by weight ratio of lubiprostone to Capryol™ PGMC is about 3:12500.

Illustrative embodiments of the present invention provide a pharmaceutical formulation described herein wherein lubiprostone is dissolved in the Capryol™ PGMC at a concentration of about 25 µg to about 1000 µg per gram.

Illustrative embodiments of the present invention provide a pharmaceutical formulation described herein wherein the at least one propylene glycol ester comprises Miglyol™ 840.

Illustrative embodiments of the present invention provide a pharmaceutical formulation described herein wherein a by weight ratio of lubiprostone to Miglyol™ 840 is between from about 1:250000 to about 1:1000.

Illustrative embodiments of the present invention provide a pharmaceutical formulation described herein wherein a by weight ratio of lubiprostone to Miglyol™ 840 is about 3:12500.

Illustrative embodiments of the present invention provide a pharmaceutical formulation described herein wherein lubiprostone is dissolved in the Miglyol™ 840 at a concentration of about 25 μg to about 1000 μg per gram.

Other aspects and features of the present invention will become apparent to those ordinarily skilled in the art upon review of the following description of specific embodiments of the invention in conjunction with the accompanying figures.

DETAILED DESCRIPTION

Illustrative embodiments of this invention provide a pharmaceutical formulation comprising lubiprostone and propylene glycol mono-ester and/or propylene glycol di-ester.

Lubiprostone is, at times, referred to as 7-[(2R,4aR,5R,7aR)-2-(1,1-difluoropentyl)-2-hydroxy-6-oxo-3,4,4a,5,7,7a-hexahydrocyclopenta[b]pyran-5-yl]heptanoic acid. Lubiprostone is a commercially available compound and routes of its synthesis are known to a person of skill in the art.

Propylene glycol mono-esters and propylene glycol di-esters are commercially available compounds that are known in the art. Routes of their synthesis are also known in the art. Monographs for such esters are available in USP32-NF27.

Propylene glycol esters suitable for use in pharmaceutical formulations of the present invention, also include mixtures of mono-esters and di-esters having a maximum mono-ester content of 80% and a di-ester content of at least 20%. For example, Propylene Glycol Monocaprylate NF27 is a commercially available mixture of propylene glycol mono-esters and di-esters of fatty acids composed primarily of caprylic acid. Such mixtures are often comprised of one of two common ratios of mono-ester to di-ester: a) 55.0%-80.0% mono-ester to 20.0%-45.0% di-ester or b) minimum 90% mono-ester to maximum 10% di-ester.

Another example of a mixture of mono-esters and di-esters is Propylene Glycol Dicaprylate/Dicaprate NF27 and this is a mixture of propylene glycol mono-esters and di-esters of caprylic acid and capric acid. The di-ester fraction is predominant in Propylene Glycol Dicaprylate/Dicaprate NF27.

Yet another example of a mixture of mono-esters and di-esters is Propylene Glycol Monolaurate NF27 and this is a mixture of propylene glycol mono-esters and di-esters of lauric acid. Such mixtures are often comprised of one of two common ratios of mono-ester to di-ester: a) 45.0%-70.0% mono-ester to 30.0%-55.0% di-ester or b) minimum 90% mono-ester to maximum 10% di-ester.

Still yet another example of a mixture of mono-esters and di-esters is Propylene Glycol Dilaurate NF27 which is a mixture of propylene glycol mono-esters and di-esters of lauric acid, with not less than 70.0% di-esters and not more than 30.0% mono-esters.

Propylene glycol monocaprylate NF27 with a mono-ester content of from 55.0% to 80.0% and a di-ester content of from 20.0% to 45.0% is commercially available under the trade name Capryol™ PGMC. Propylene glycol monocaprylate NF27 with a minimum mono-ester content of 90% and a maximum di-ester content of 10% is available under the trade name Capryol™ 90.

Propylene glycol monolaurate NF27 with a mono-ester content of from 45.0% to 70.0% and a di-ester content of from 30.0% to 55.0% is commercially available under the trade name Lauroglycol™ FCC. Propylene glycol monolaurate NF27 with a minimum mono-ester content of 90% and a maximum di-ester content of 10% is available under the trade name Lauroglycol™ 90.

Miglyol™ 840 is a propylene glycol diester of plant fatty acids with chain lengths of 8 carbon atoms to 10 carbon atoms. Miglyol™ 840 has a composition of fatty acids that include a maximum of 2 parts Caprylic acid ($C_{6:0}$), from 65 parts to 80 parts Caprylic acid ($C_{8:0}$), from 20 parts to 35 parts Capric acid, maximum 2 parts Lauric acid, and maximum 1 part Myristic acid ($C_{14:0}$).

Lubiprostone is known in the art to be a relatively unstable compound. Pharmaceutical formulations comprising lubiprostone must stabilize lubiprostone in a manner that preserves the lubiprostone. Furthermore, pharmaceutical formulations comprising lubiprostone must solubilize the lubiprostone. The Examples below provide evidence that lubiprostone is soluble in some lipophilic solvents and not in others. Furthermore, lubiprostone is not stable in some lipophilic solvents, stable in some other lipophilic solvents, and yet more stable in other lipophilic solvents. The Examples below show that lubiprostone is suitably soluble in propylene glycol mono-esters and in propylene glycol di-esters. The Examples below also show that lubiprostone is particularly stable in propylene glycol mono-esters and propylene glycol di-esters. Miglyol™ 840 is a particular mixture of propylene glycol di-esters that lubiprostone is particularly stable in. The Examples below provide evidence that lubiprostone is more stable in formulations comprising Miglyol™ 840 than other formulations not having Miglyol™ 840 under the stability stress conditions set out in the Examples below.

Pharmaceutical formulations of the present invention will have between about 25 μg to about 1000 μg of lubiprostone dissolved in each gram of pharmaceutical formulation. Hence, a suitable by weight ratio of lubiprostone to propylene glycol mono- and/or di-ester is between about 1:250000 to about 1:1000. In some embodiments the by weight ratio of lubiprostone to propylene glycol mono- and/or di-ester is: about 1:12500 to about 1:4000; about 1:12500 to about 3:12500; and about 3:12500 to about 1:4000. Often, the ratio of lubiprostone to propylene glycol mono- and/or di-ester is about 3:12500.

For example, if propylene glycol monocaprylate is the only propylene glycol mono-ester in the pharmaceutical formulation, suitable by weight ratios of lubiprostone to propylene glycol monocaprylate include between from about 1:250000 to about 1:1000; between from about 1:12500 to about 1:4000; between from about 1:12500 to about 3:12500; between from about 3:12500 to about 1:4000; and about 3:12500.

As used herein, the term "by weight ratio" means the values in the ratio are expressed in terms of gross weight. For example, if 25 μg of lubiprostone is dissolved in 100 mg of propylene glycol monocaprylate, then the by weight ratio of lubiprostone to propylene glycol monocaprylate in such a formulation would be 1:4000.

As used herein, the word "about" means that exact adherence to the exact numerical value or numerical range following the word is not strictly necessary. Minor deviations from the exact numerical value and/or range are permitted. In general a deviation of ±5% is acceptable.

Pharmaceutical formulations according to the present invention may be enveloped with a gelatin capsule, either a soft gelatin capsule or a two-piece hard gelatin capsule. The two piece hard gelatin capsule may be sealed. Such capsules provide for additional stability of the lubiprostone in pharmaceutical formulations of the present invention. Sealing the capsules provides for even more stability of the lubiprostone in pharmaceutical formulations of the present invention. Suitable capsules are known to a person of skill in the art.

EXAMPLES

The following examples are illustrative of some of the embodiments of the invention described herein. These examples should not be considered to limit the spirit or scope of the invention in any way.

As used in the Examples below, the term "RT" stands for room temperature and the term "RH" stands for relative humidity.

Example 1

TABLE 1

| Ingredient | Quantity |
| --- | --- |
| Lubiprostone | 2.5 mg |
| Oleic Acid | 10.4 g |

2.5 mg of Lubiprostone was dispensed using a small spatula into a small piece of folded paper on a microbalance. The lubiprostone was then transferred into a small glass vial. The oleic acid was then added to the glass vial and the vial was closed with a cap. The closed vial was then tumbled to aid dissolution of the lubiprostone in the oleic acid.

It took 1 hour and 50 minutes for the lubiprostone to completely dissolve in the oleic acid.

Some stability tests were carried out on this solution and the results were of limited value due to a technical problem. Nevertheless, the results, despite the technical problem, showed that the stability of lubiprostone in oleic acid was poor.

Example 2

TABLE 2

| Ingredient | Quantity |
| --- | --- |
| Lubiprostone | 2.5 mg |
| Capryol ™ PGMC | 10.4 g |

2.5 mg of Lubiprostone was dispensed using a small spatula into a small piece of folded paper on a microbalance. The lubiprostone was then transferred into a small glass vial. The Capryol™ PGMC was then added to the glass vial and the vial was closed with a cap. The closed vial was then tumbled to aid dissolution of the lubiprostone in the Capryol™ PGMC.

It took 1 minute for the lubiprostone to completely dissolve in the Capryol™ PGMC.

Some stability tests were carried out on this solution and the results were of limited value due to a technical problem. Nevertheless, the results, despite the technical problem, showed that the stability of lubiprostone in Capryol™ PGMC warranted further experimentation.

A second solution of lubiprostone dissolved in Capryol™ PGMC was prepared and then subjected to a number of stress conditions, the details of which are set out below. The second solution was prepared in the same manner as described above and 2.5 mg of lubiprostone was dissolved in 10.4 g of Capryol™ PGMC. After the samples were subjected to the stress conditions, the samples were then analyzed using HPLC methods to determine an amount of degradation of the lubiprostone after stressing. The results are shown in Table 2.1 below.

Samples of the second solution were stored in the test tubes under the following conditions:

Initial: no stressing or significant time lapse occurred prior to high performance liquid chromatography (HPLC) analysis.

RT/1 week: 1 test tube of solution was kept at room temperature on a shelf and protected from light for 1 week. The test tube was closed with a cap.

40 C/1 week: 1 test tube of solution was kept at 40° C. in a stress chamber for 1 week. The tube was closed with a cap.

60 C/1 week: 1 test tube of solution was kept at 60° C. in a stress chamber for 1 week. The test tube was closed with a cap.

40 C/75% RH/1 week/open: 1 test tube of solution was kept at 40° C. and at 75% relative humidity in a stress chamber for 1 week. The test tube was not closed with a cap.

40 C/75% RH/1 week/closed: 1 test tube of solution was kept at 40° C. and at 75% relative humidity in a stress chamber for 1 week. The test tube was closed with a cap.

RT/2 weeks: 1 test tube of solution was kept at room temperature on a shelf and protected from light for 2 weeks. The test tube was closed with a cap.

40 C/2 weeks: 1 test tube of solution was kept at 40° C. in a stress chamber for 2 weeks. The test tube was closed with a cap.

60 C/2 weeks: 1 test tube of solution was kept at 60° C. in a stress chamber for 2 weeks. The test tube was closed with a cap.

40 C/75% RH/2 weeks/open: 1 test tube of solution was kept at 40° C. and at 75% relative humidity in a stress chamber for 2 weeks. The test tube was not closed with a cap.

40 C/75% RH/2 weeks/closed: 1 test tube of solution was kept at 40° C. and at 75% relative humidity in a stress chamber for 2 weeks. The test tube was closed with a cap.

TABLE 2.1

| Stress Conditions | % Total Degradation |
| --- | --- |
| Initial | 0.02 |
| RT/1 week | 0.05 |
| 40 C./1 week | 0.12 |
| 60 C./1 week | 0.49 |
| 40 C./75% RH/1 week/open | 0.31 |
| 40 C./75% RH/1 week/closed | 0.17 |
| RT/2 weeks | 0.09 |
| 40 C./2 weeks | 0.16 |
| 60 C./2 weeks | 0.97 |
| 40 C./75% RH/2 weeks/open | 0.67 |
| 40 C./75% RH/2 weeks/closed | 0.45 |

Example 3

TABLE 3

| Ingredient | Quantity |
| --- | --- |
| Lubiprostone | 2.5 mg |
| Lauroglycol™ FCC | 10.4 g |

2.5 mg of Lubiprostone was dispensed using a small spatula into a small piece of folded paper on a microbalance. The lubiprostone was then transferred into a small glass vial. The Lauroglycol™ FCC was then added to the glass vial and the vial was closed with a cap. The closed vial was then tumbled to aid dissolution of the lubiprostone in the Lauroglycol™ FCC.

It took 6 minutes for the lubiprostone to completely dissolve in the Lauroglycol™ FCC.

Some stability tests were carried out on this solution and the results were of limited value due to a technical problem. Nevertheless, the results, despite the technical problem, showed that the stability of lubiprostone in Lauroglycol™ FCC warranted further experimentation.

A second solution of lubiprostone dissolved in Lauroglycol™ FCC was prepared and then subjected to a number of stress conditions, the details of which are set out in Example 2 above. The second solution was prepared in the same manner as described above and 2.5 mg of lubiprostone was dissolved in 10.4 g of Lauroglycol™ FCC. After the samples were subjected to the stress conditions, the samples were then analyzed using HPLC methods to determine an amount of degradation of the lubiprostone after stressing. The results are shown in Table 3.1 below.

TABLE 3.1

| Stress Conditions | % Total Degradation |
| --- | --- |
| Initial | 0.02 |
| RT/1 week | 0.05 |
| 40 C./1 week | 0.09 |
| 60 C./1 week | 0.43 |
| 40 C./75% RH/1 week/open | 0.33 |
| 40 C./75% RH/1 week/closed | 0.28 |
| RT/2 weeks | 0.10 |
| 40 C./2 weeks | 0.15 |
| 60 C./2 weeks | 1.18 |
| 40 C./75% RH/2 weeks/open | 0.60 |
| 40 C./75% RH/2 weeks/closed | 0.59 |

Example 4

TABLE 4

| Ingredient | Quantity |
| --- | --- |
| Lubiprostone | 2.5 mg |
| Benzyl Alcohol | 10.4 g |

2.5 mg of Lubiprostone was dispensed using a small spatula into a small piece of folded paper on a microbalance. The lubiprostone was then transferred into a small glass vial. The benzyl alcohol was then added to the glass vial and the vial was closed with a cap. The closed vial was then tumbled to aid dissolution of the lubiprostone in the benzyl alcohol.

It took 1 minute for the lubiprostone to completely dissolve in the benzyl alcohol.

Some stability tests were carried out on this solution and the results were of limited value due to a technical problem. Nevertheless, the results, despite the technical problem, showed that the stability of lubiprostone in benzyl alcohol was poor.

Example 5

TABLE 5

| Ingredient | Quantity |
| --- | --- |
| Lubiprostone | 2.5 mg |
| Mineral Oil | 10.4 g |

2.5 mg of Lubiprostone was dispensed using a small spatula into a small piece of folded paper on a microbalance. The lubiprostone was then transferred into a small glass vial. The mineral oil was then added to the glass vial and the vial was closed with a cap. The closed vial was then tumbled to aid dissolution of the lubiprostone in the mineral oil.

The lubiprostone did not completely dissolve in the mineral oil.

Example 6

TABLE 6

| Ingredient | Quantity |
| --- | --- |
| Lubiprostone | 2.5 mg |
| Simethicone | 10.4 g |

2.5 mg of Lubiprostone was dispensed using a small spatula into a small piece of folded paper on a microbalance. The lubiprostone was then transferred into a small glass vial. The simethicone was then added to the glass vial and the vial was closed with a cap. The closed vial was then tumbled to aid dissolution of the lubiprostone in the simethicone.

The lubiprostone did not completely dissolve in the simethicone.

Example 7

TABLE 7

| Ingredient | Quantity |
| --- | --- |
| Lubiprostone | 2.5 mg |
| Dibutyl Phalate | 10.4 g |

2.5 mg of Lubiprostone was dispensed using a small spatula into a small piece of folded paper on a microbalance. The lubiprostone was then transferred into a small glass vial. The dibutyl phalate was then added to the glass vial and the vial was closed with a cap. The closed vial was then tumbled to aid dissolution of the lubiprostone in the dibutyl phalate.

It took 10 minutes for the lubiprostone to completely dissolve in the dibutyl phalate.

Some stability tests were carried out on this solution and the results were of limited value due to a technical problem.

Nevertheless, the results, despite the technical problem, showed that the stability of lubiprostone in dibutyl phalate was poor.

Example 8

TABLE 8

| Ingredient | Quantity |
| --- | --- |
| Lubiprostone | 2.5 mg |
| Dibutyl Sebecate | 10.4 g |

2.5 mg of Lubiprostone was dispensed using a small spatula into a small piece of folded paper on a microbalance. The lubiprostone was then transferred into a small glass vial. The dibutyl sebecate was then added to the glass vial and the vial was closed with a cap. The closed vial was then tumbled to aid dissolution of the lubiprostone in the dibutyl sebecate.

It took 10 minutes for the lubiprostone to completely dissolve in the dibutyl sebecate.

Some stability tests were carried out on this solution and the results were of limited value due to a technical problem. Nevertheless, the results, despite the technical problem, showed that the stability of lubiprostone in dibutyl sebecate was poor.

Example 9

TABLE 9

| Ingredient | Quantity |
| --- | --- |
| Lubiprostone | 2.5 mg |
| Triethyl Citrate | 10.4 g |

2.5 mg of Lubiprostone was dispensed using a small spatula into a small piece of folded paper on a microbalance. The lubiprostone was then transferred into a small glass vial. The triethyl citrate was then added to the glass vial and the vial was closed with a cap. The closed vial was then tumbled to aid dissolution of the lubiprostone in the triethyl citrate.

It took 10 minutes for the lubiprostone to completely dissolve in the triethyl citrate.

Example 10

TABLE 10

| Ingredient | Quantity |
| --- | --- |
| Lubiprostone | 2.5 mg |
| Span ™ 20 | 10.4 g |

2.5 mg of Lubiprostone was dispensed using a small spatula into a small piece of folded paper on a microbalance. The lubiprostone was then transferred into a small glass vial. The Span™ 20 was then added to the glass vial and the vial was closed with a cap. The closed vial was then tumbled to aid dissolution of the lubiprostone in the Span™ 20.

The lubiprostone did not completely dissolve in the Span™ 20.

Example 11

TABLE 11

| Ingredient | Quantity |
| --- | --- |
| Lubiprostone | 2.5 mg |
| Span ™ 80 | 10.4 g |

2.5 mg of Lubiprostone was dispensed using a small spatula into a small piece of folded paper on a microbalance. The lubiprostone was then transferred into a small glass vial. The Span™ 80 was then added to the glass vial and the vial was closed with a cap. The closed vial was then tumbled to aid dissolution of the lubiprostone in the Span™ 80.

It took 12 minutes for the lubiprostone to completely dissolve in the Span™ 80.

Example 12

TABLE 12

| Ingredient | Quantity |
| --- | --- |
| Lubiprostone | 2.5 mg |
| Capryol ™ 90 | 10.4 g |

2.5 mg of Lubiprostone was dispensed using a small spatula into a small piece of folded paper on a microbalance. The lubiprostone was then transferred into a small glass vial. The Capryol™ 90 was then added to the glass vial and the vial was closed with a cap. The closed vial was then tumbled to aid dissolution of the lubiprostone in the Capryol™ 90. The lubiprostone completely dissolved in the Capryol™ 90.

Some stability tests were carried out on this solution and the results were of limited value due to a technical problem. Nevertheless, the results, despite the technical problem, showed that the stability of lubiprostone in Capryol™ 90 warranted further experimentation.

A second solution of lubiprostone dissolved in Capryol™ 90 was prepared and then subjected to a number of stress conditions, the details of which are set out in Example 2 above. The second solution was prepared in the same manner as described above and 2.5 mg of lubiprostone was dissolved in 10.4 g of Capryol™ 90. After the samples were subjected to the stress conditions, the samples were then analyzed using HPLC methods to determine an amount of degradation of the lubiprostone after stressing. The results are shown in Table 12.1 below.

TABLE 12.1

| Stress Conditions | % Total Degradation |
| --- | --- |
| Initial | 0.02 |
| RT/1 week | 0.05 |
| 40 C./1 week | 0.56 |
| 60 C./1 week | 1.00 |
| 40 C./75% RH/1 week/open | 0.53 |
| 40 C./75% RH/1 week/closed | 0.44 |
| RT/2 weeks | 0.13 |
| 40 C./2 weeks | 0.38 |
| 60 C./2 weeks | 1.42 |
| 40 C./75% RH/2 weeks/open | 0.88 |
| 40 C./75% RH/2 weeks/closed | 0.76 |

Example 13

TABLE 13

| Ingredient | Quantity |
| --- | --- |
| Lubiprostone | 2.5 mg |
| Lauroglycol ™ 90 | 10.4 g |

2.5 mg of Lubiprostone was dispensed using a small spatula into a small piece of folded paper on a microbalance. The lubiprostone was then transferred into a small glass vial. The Lauroglycol™ 90 was then added to the glass vial and the vial was closed with a cap. The closed vial was then tumbled to aid dissolution of the lubiprostone in the Lauroglycol™ 90. The lubiprostone completely dissolved in the Lauroglycol™ 90.

Some stability tests were carried out on this solution and the results were of limited value due to a technical problem. Nevertheless, the results, despite the technical problem, showed that the stability of lubiprostone in Lauroglycol™ 90 warranted further experimentation.

A second solution of lubiprostone dissolved in Lauroglycol™ 90 was prepared and then subjected to a number of stress conditions, the details of which are set out in Example 2 above. The second solution was prepared in the same manner as described above and 2.5 mg of lubiprostone was dissolved in 10.4 g of Lauroglycol™ 90. After the samples were subjected to the stress conditions, the samples were then analyzed using HPLC methods to determine an amount of degradation of the lubiprostone after stressing. The results are shown in Table 13.1 below.

TABLE 13.1

| Stress Conditions | % Total Degradation |
| --- | --- |
| Initial | 0.02 |
| RT/1 week | 0.05 |
| 40 C./1 week | 0.30 |
| 60 C./1 week | 5.34 |
| 40 C./75% RH/1 week/open | 0.62 |
| 40 C./75% RH/1 week/closed | 0.35 |
| RT/2 weeks | 0.11 |
| 40 C./2 weeks | 0.63 |
| 60 C./2 weeks | 13.75 |
| 40 C. 75% RH/2 weeks/open | 1.26 |
| 40 C./75% RH/2 weeks/closed | 0.75 |

Example 14

TABLE 14

| Ingredient | Quantity |
| --- | --- |
| Lubiprostone | 25 µg |
| Captex ™ 355 | 100 mg |

25 µg of Lubiprostone was dispensed into a small glass vial. The Captex™ 355 was then added to the glass vial and the vial was closed with a cap. The closed vial was then tumbled to aid dissolution of the lubiprostone in the Captex™ 355. The lubiprostone completely dissolved in the Captex™ 355.

Some stability tests were carried out on this solution and the results were of limited value due to a technical problem. Nevertheless, the results, despite the technical problem, showed that the stability of lubiprostone in Captex™ 355 warranted further experimentation.

A second solution of lubiprostone dissolved in Captex™ 355 was prepared and then subjected to a number of stress conditions, the details of which are set out in Example 2 above. The second solution was prepared in the same manner as described above and 25 µg of lubiprostone was dissolved in 104 mg of Captex™ 355. After the samples were subjected to the stress conditions, the samples were then analyzed using HPLC methods to determine an amount of degradation of the lubiprostone after stressing. The results are shown in Table 14.1 below.

TABLE 14.1

| Stress Conditions | % Total degradation |
| --- | --- |
| non-stress | 0.05 |
| Initial | 0.00 |
| RT/2 weeks | 0.12 |
| 40 C./2 weeks | 0.59 |
| 60 C./2 weeks | 2.44 |
| 40 C./75% RH/2 weeks/open | 5.75 |
| 40 C./75% RH/2 weeks/closed | 4.64 |

Example 15

TABLE 15

| Ingredient | Quantity |
| --- | --- |
| Lubiprostone | 25 µg |
| Vitamin E | 100 mg |

25 µg of Lubiprostone was dispensed into a small glass vial. The vitamin E was then added to the glass vial and the vial was closed with a cap. The closed vial was then tumbled to aid dissolution of the lubiprostone in the Vitamin E. The lubiprostone completely dissolved in the Vitamin E.

Some stability tests were carried out on this solution and the results were of limited value due to a technical problem. Nevertheless, the results, despite the technical problem, showed that the stability of lubiprostone in Vitamin E was poor.

Example 16

TABLE 16

| Ingredient | Quantity |
| --- | --- |
| Lubiprostone | 25 µg |
| Miglyol ™ 840 | 100 mg |

25 µg of Lubiprostone was dispensed into a small glass vial. The Miglyol™ 840 was then added to the glass vial and the vial was closed with a cap. The closed vial was then tumbled to aid dissolution of the lubiprostone in the Miglyol™ 840. The lubiprostone completely dissolved in the Miglyol™ 840.

A solution of lubiprostone dissolved in Miglyol™ 840 were subjected to a number of stress conditions, the details of which are set out in Example 2 above. The second solution was prepared in the same manner as described above and 25 µg of lubiprostone was dissolved in 104 mg of Miglyol™ 840. After the samples were subjected to the stress conditions, the samples were then analyzed using HPLC methods to determine an amount of degradation of the lubiprostone after stressing. The results are shown in Table 3.1 below.

TABLE 16.1

| Stress Conditions | % Total degradation |
|---|---|
| Initial | 0.00 |
| RT/1 week | 0.08 |
| 40 C./1 week | 0.11 |
| 60 C./1 week | 0.32 |
| 40 C./75% RH/1 week/open | 0.53 |
| 40 C./75% RH/1 week/closed | 0.39 |

Example 17

Samples, in the form of capsules, of the formulation sold under the trade name Amitiza™ were obtained and were subjected to a number of stress conditions, the details of which are set out below. After the samples were subjected to the stress conditions, the samples were then analyzed using HPLC methods to determine an amount of degradation of the lubiprostone after stressing. The results are shown in Table 17.1 below.

Capsules of Amitiza™ were subjected to the following stress conditions:

RT/whole/4 weeks: 1 test tube containing a whole, unbroken capsule was kept at room temperature on a shelf and protected from light for 4 weeks. The test tube was closed with a cap;

60 C/whole/4 weeks: 1 test tube containing a whole, unbroken capsule was kept at 60° C. in a stress chamber for 4 weeks. The test tube was closed with a cap.

40 C/75% RH/whole/4 weeks/open: 1 test tube containing a whole, unbroken capsule was kept at 40° C. and at 75% relative humidity in a stress chamber for 4 weeks. The test tube was not closed with a cap.

RT/whole/6 weeks: 1 test tube containing a whole, unbroken capsule was kept at room temperature on a shelf and protected from light for 6 weeks. The test tube was closed with a cap.

RT/crushed/2 weeks: 1 test tube containing a crushed capsule was kept at room temperature on a shelf and protected from light for 2 weeks. The test tube was closed with a cap.

60 C/whole/6 weeks: 1 test tube containing a whole, unbroken capsule was kept at 60° C. in a stress chamber for 6 weeks. The test tube was closed with a cap.

60 C/crushed/2 weeks: 1 test tube containing a crushed capsule was kept at 60° C. in a stress chamber for 2 weeks. The test tube was closed with a cap.

40 C/75% RH/whole/6 weeks/open: 1 test tube containing a whole, unbroken capsule was kept at 40° C. and at 75% relative humidity in a stress chamber for 6 weeks. The test tube was not closed with a cap.

40 C/75% RH/crushed/2 weeks/open: 1 test tube containing a crushed capsule was kept at 40° C. and at 75% relative humidity in a stress chamber for 2 weeks. The test tube was not closed with a cap.

TABLE 17.1

| Stress Conditions | % Total degradation |
|---|---|
| RT/whole/4 weeks | 0.17 |
| 60 C./whole/4 weeks | 0.33 |
| 40 C./75% RH/whole/4 weeks/open | 0.46 |
| RT/whole/6 weeks | 0.21 |
| RT/crushed/2 weeks | 0.26 |
| 60 C./whole/6 weeks | 0.37 |
| 60 C./crushed/2 weeks | 1.65 |
| 40 C./75% RH/whole/6 weeks/open | 1.81 |
| 40 C./75% RH/crushed/2 weeks/open | 2.03 |

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A pharmaceutical formulation comprising lubiprostone and a propylene glycol ester, wherein the propylene glycol ester is a mixture of propylene glycol di-ester of caprylic acid and propylene glycol di-ester of capric acid, and the mixture has a di-ester content greater than its mono-ester content.

2. The pharmaceutical formulation of claim 1 wherein a by weight ratio of lubiprostone to propylene glycol ester is between from about 1:250,000 to about 1:1,000.

3. The pharmaceutical formulation of claim 1 wherein a by weight ratio of lubiprostone to propylene glycol ester is about 3:12,500.

4. The pharmaceutical formulation of claim 1 wherein lubiprostone is dissolved in the propylene glycol ester at a concentration of about 25 μg to about 1,000 μg per gram.

5. The pharmaceutical formulation of claim 1, wherein a by weight ratio of lubiprostone to propylene glycol ester is about 1:4,000.

6. The pharmaceutical formulation of claim 1, wherein the mixture of propylene glycol di-ester of caprylic acid and propylene glycol di-ester of capric acid comprises Propylene Glycol Dicaprylate/Dicaprate NF27.

7. The pharmaceutical formulation of claim 6, wherein a by weight ratio of lubiprostone to propylene glycol ester is about 1:4,000.

* * * * *